United States Patent

Desos et al.

(10) Patent No.: US 7,268,130 B2
(45) Date of Patent: Sep. 11, 2007

(54) BENZOTHIADIAZINE COMPOUNDS

(75) Inventors: Patrice Desos, Bois-Colombes (FR);
Alexis Cordi, Suresnes (FR); Pierre Lestage, La Celle-Saint-Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 20 days.

(21) Appl. No.: 11/265,011

(22) Filed: Nov. 2, 2005

(65) Prior Publication Data

US 2006/0094712 A1    May 4, 2006

(51) Int. Cl.
*C07D 285/22* (2006.01)
*A61K 31/5415* (2006.01)
*A61P 25/24* (2006.01)

(52) U.S. Cl. .................................. 514/223.2; 544/12

(58) Field of Classification Search ............... 544/12; 514/223.2
See application file for complete search history.

(56) References Cited

OTHER PUBLICATIONS

Alt et al. Current Pharmaceutical Design, 2005, 11, 1511-1527.*
Black et al Psychopharmacology (2005) 179: 154-163.*

* cited by examiner

*Primary Examiner*—Kahsay Habte
(74) *Attorney, Agent, or Firm*—Hueschen and Sage

(57) ABSTRACT

The invention relates to compounds of formula (I):

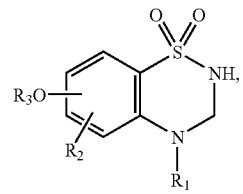

wherein:
$R_1$ represents alkyl substituted by one or more halogen atoms,
$R_2$ represents hydrogen, halogen or hydroxy,
$R_3$ represents unsubstituted or substituted aryl, their isomers, and also addition salts thereof.
and medicinal products containing the same which are useful in treating or preventing disorders associated with AMPA flux.

10 Claims, No Drawings

BENZOTHIADIAZINE COMPOUNDS

FIELD OF THE INVENTION

The present invention relates to new benzothiadiazine compounds. The compounds of the present invention are new and have very valuable pharmacologic characteristics as AMPA modulators.

BACKGROUND OF THE INVENTION

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, innumerable works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

In the literature, compounds having a benzamide structure have been described as possessing this same mechanism of action and as improving memory performance (Synapse, 1993, 15, 326-329). Compound BA 74, in particular, is the most active of those new pharmacological agents.

Finally, the patent specification EP 692 484 describes a benzothiadiazine compound having facilitating activity on the AMPA current, and the patent application WO 99/42456 describes, inter alia, certain benzothiadiazine compounds as modulators of AMPA receptors.

The benzothiadiazine compounds to which the present invention relates, besides being new, surprisingly exhibit especially valuable pharmacological activity on the AMPA current. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the sequelae of acute neurodegenerative diseases, with the sequelae of ischaemia and with the sequelae of epilepsy.

DETAILED DESCRIPTION OF THE INVENTION

More specifically, the present invention relates to compounds of formula (I):

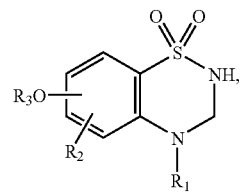

wherein:
$R_1$ represents a linear or branched $(C_1-C_6)$alkyl group substituted by one or more halogen atoms,
$R_2$ represents a hydrogen atom, a halogen atom or a hydroxy group,
$R_3$ represents an unsubstituted aryl group or an aryl group substituted by one or more identical or different groups selected from:
linear or branched $(C_1-C_6)$alkyl; linear or branched $(C_1-C_6)$alkoxy; linear or branched $(C_1-C_6)$polyhaloalkyl; halogen atoms; linear or branched $(C_1-C_6)$alkoxy-carbonyl; linear or branched $(C_1-C_6)$alkylthio; carboxy; linear or branched $(C_1-C_6)$acyl; linear or branched $(C_1-C_6)$polyhaloalkoxy; hydroxy; cyano; nitro; amidino (optionally substituted by one or two identical or different groups selected from linear or branched $(C_1-C_6)$alkyl, hydroxy, linear or branched $(C_1-C_6)$alkoxy and

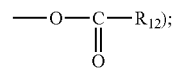

amino (optionally substituted by one or two linear or branched $(C_1-C_6)$alkyl groups); aminocarbonyl (optionally substituted by one or two linear or branched $(C_1-C_6)$alkyl groups); benzyloxy; $(C_1-C_6)$alkylsulphonylamino (optionally substituted on the nitrogen by a linear or branched $(C_1-C_6)$alkyl group); (trifluoromethylsulphonyl)amino; a heterocyclic group; and linear or branched $(C_1-C_6)$alkyl on the one hand substituted by one or more identical or different groups selected from hydrogen and halogen atoms and linear or branched $(C_1-C_6)$alkyl groups and on the other hand substituted by a group selected from $NR_4R_5$, $S(O)_nR_6$, $OR_7$, amidino (optionally substituted by one or two identical or different groups selected from linear or branched $(C_1-C_6)$ alkyl, hydroxy, linear or branched $(C_1-C_6)$alkoxy and

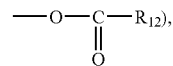

and a heterocyclic group, wherein:
$R_4$ represents a hydrogen atom or a linear or branched $(C_1-C_6)$alkyl, $S(O)_pR_8$, $COR_9$ or $P(O)(OR_{10})(OR_{11})$ group,
$R_5$ represents a hydrogen atom or a linear or branched $(C_1-C_6)$alkyl group,
or $R_4$ and $R_5$, together with the nitrogen atom carrying them, form a heterocyclic group,
$R_6$, $R_8$, $R_9$, $R_{10}$, $R_{11}$ and $R_{12}$, which may be the same or different, each represent a hydrogen atom or a linear or branched (C₁-C₆)alkyl group optionally substituted by one or more halogen atoms; an aryl-(C₁-C₆)alkyl group in which the alkyl moiety is linear or branched; or an aryl group, R₇ represents a linear or branched (C₁-C₆)alkyl group or a linear or branched (C₁-C₆)acyl group, n and p, which may be the same or different, each represent 0, 1 or 2, to their enantiomers and diastereoisomers, and also to addition salts thereof with a pharmaceutically acceptable acid or base, it being understood that:

a heterocyclic group means a monocyclic or bicyclic, aromatic or non-aromatic group containing from one to four identical or different hetero atoms selected from nitrogen, oxygen and sulphur, optionally substituted by one or more identical or different groups selected from halogen, linear or branched (C₁-C₆)alkyl, linear or branched (C₁-C₆)alkoxy, linear or branched (C₁-C₆)polyhaloalkyl, linear or branched (C₁-C₆)alkoxy-carbonyl, oxo, thioxo, carboxy, linear or branched (C₁-C₆)acyl, linear or branched (C₁-C₆)polyhaloalkoxy, hydroxy, cyano, nitro, amino (optionally substituted by one or more linear or branched (C₁-C₆)alkyl groups), aminosulphonyl (optionally substituted by one or more linear or branched (C₁-C₆)alkyl groups) and (C₁-C₆) alkylsulphonylamino, an aryl group means a monocyclic aromatic group or a bicyclic group in which at least one of the rings is aromatic, optionally substituted by one or more identical or different groups selected from halogen, linear or branched (C₁-C₆) alkyl (optionally substituted by one or more hydroxy groups), linear or branched (C₁-C₆)alkoxy, linear or branched (C₁-C₆)polyhaloalkyl, linear or branched (C₁-C₆) alkoxy-carbonyl, oxo, thioxo, linear or branched (C₁-C₆) alkylthio, carboxy, linear or branched (C₁-C₆)acyl, linear or branched (C₁-C₆)polyhaloalkoxy, hydroxy, cyano, nitro, amino (optionally substituted by one or more linear or branched (C₁-C₆)alkyl or linear or branched (C₁-C₆)acyl groups), aminocarbonyl (optionally substituted by one or more linear or branched (C₁-C₆)alkyl groups), aminosulphonyl (optionally substituted by one or more linear or branched (C₁-C₆)alkyl groups), mono- or di-((C₁-C₆)alkylsulphonyl)amino, mono- or di-(trifluoromethylsulphonyl) amino, PO(OR_a)(OR_b) (wherein R_a and R_b, which may be the same or different, each represent a hydrogen atom or a linear or branched (C₁-C₆)alkyl group), benzyloxy and phenyl (optionally substituted by one or more identical or different groups selected from halogen, linear or branched (C₁-C₆)alkyl, linear or branched (C₁-C₆)perhaloalkyl, hydroxy and linear or branched (C₁-C₆)alkoxy).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preference is given to the group R₁ being haloethyl such as fluoroethyl, chloroethyl or bromoethyl, more preferably fluoro- or chloro-ethyl.

R₂ preferably represents a hydrogen atom.

Preference is given to the group R₃ being a phenyl or substituted phenyl group, more especially substituted by:

an amidino group, a hydroxyamidino group, an alkoxy group, an alkylsulphonylamino group optionally substituted on the nitrogen by an alkyl group, or an alkyl group substituted by an amidino, hydroxyamidino, OR₇, NHS(O)_pR₈ or NHCOR₉ group.

Even more especially, the invention relates to compounds of formula (I) which are:

N-(4-{[4-(2-bromoethyl)-1,1-dioxido-3,4-dihydro-2H-1,2,4-benzothiadiazin-7-yl]oxy}benzyl)methanesulphonamide, N-(4-{[4-(2-fluoroethyl)-1,1-dioxido-3,4-dihydro-2H-1,2,4-benzothiadiazin-7-yl]oxy}benzyl)methanesulphonamide, N-(4-{[4-(2-chloroethyl)-1,1-dioxido-3,4-dihydro-2H-1,2,4-benzothiadiazin-7-yl]oxy}benzyl)methanesulphonamide, N-(3-{[4-(2-fluoroethyl)-1,1-dioxido-3,4-dihydro-2H-1,2,4-benzothiadiazin-7-yl]oxy}phenyl)methanesulphonamide, N-(4-{[4-(2-fluoroethyl)-1,1-dioxido-3,4-dihydro-2H-1,2,4-benzothiadiazin-7-yl]oxy}phenyl)methanesulphonamide, 4-(2-fluoroethyl)-7-(3-methoxyphenoxy)-3,4-dihydro-2H-1,2,4-benzothiadiazine 1,1-dioxide, N-(3-{[4-(2-fluoroethyl)-1,1-dioxido-3,4-dihydro-2H-1,2,4-benzothiadiazin-7-yl]oxy}-benzyl)acetamide, N-(3-{[4-(2-fluoroethyl)-1,1-dioxido-3,4-dihydro-2H-1,2,4-benzothiadiazin-7-yl]oxy}-benzyl)methanesulphonamide, N-(4-{[4-(2-fluoroethyl)-1,1-dioxido-3,4-dihydro-2H-1,2,4-benzothiadiazin-7-yl]oxy}-benzyl)-N-methylmethanesulphonamide, 4-(2-fluoroethyl)-7-phenoxy-3,4-dihydro-2H-1,2,4-benzothiadiazine 1,1-dioxide, 3-{[4-(2-fluoroethyl)-1,1-dioxido-3,4-dihydro-2H-1,2,4-benzothiadiazin-7-yl]oxy}-N'-hydroxybenzenecarboximidamide, and 3-{[4-(2-fluoroethyl)-1,1-dioxido-3,4-dihydro-2H-1,2,4-benzothiadiazin-7-yl]oxy}-N-methylbenzamide.

The invention relates also to a process for the preparation of compounds of formula (I), which process is characterised in that there is used as starting material the compound of formula (II):

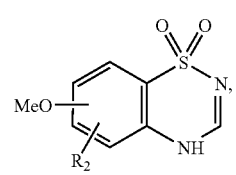

(II)

wherein R₂ is as defined in formula (I), with which there is condensed, in a basic medium, a linear or branched (C₁-C₆)haloalkyl bearing an hydroxy group, which is then converted into a corresponding halogenated compound to yield compound of formula (III):

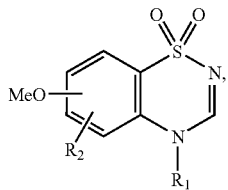
(III)

wherein $R_1$ and $R_2$ are as defined for formula (I), which is subjected to a demethylation reaction, in the presence of $BBr_3$ or $BF_3$, for example, to yield the compound of formula (V):

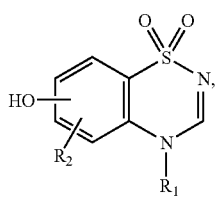
(IV)

wherein $R_1$ and $R_2$ are as defined hereinbefore, with which there is condensed, in the presence of $Cu(OAc)_2$, the boronic acid compound of formula (V):

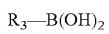
(V), wherein $R_3$ is as defined for formula (I), to yield the compound of formula (VI):

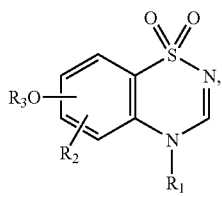
(VI)

wherein $R_1$, $R_2$ and $R_3$ are as defined hereinbefore, which is subjected to reduction with $NaBH_4$, for example, to yield the compound of formula (I):

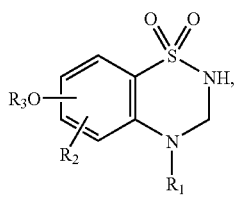
(I)

wherein $R_1$, $R_2$ and $R_3$ are as defined hereinbefore, or which compound of formula (III) is subjected to reduction, in the presence of $NaBH_4$, for example, to obtain the compound of formula (VII):

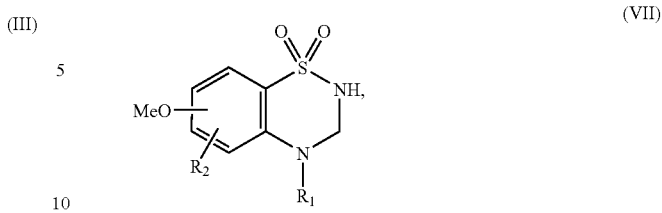
(VII)

wherein $R_1$ and $R_2$ are as defined hereinbefore, which is subjected to a demethylation reaction, in the presence of $BBr_3$ or $BF_3$, for example, to yield the compound of formula (VIII):

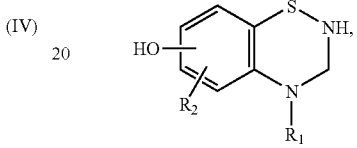
(VIII)

wherein $R_1$ and $R_2$ are as defined hereinbefore, with which there is condensed, in the presence of $Cu(OAc)_2$, the boronic acid compound of formula (V) as defined hereinbefore to yield the compound of formula (I), which compound of formula (I) is purified, if necessary, according to a conventional purification technique, is separated, where appropriate, into its isomers according to a conventional separation technique and is converted, if desired, into its addition salts with a pharmaceutically acceptable acid or base.

The invention relates also to the compound of formula (VIII):

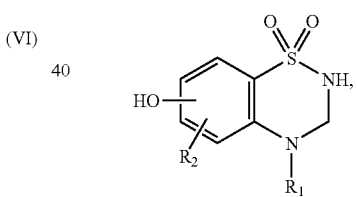
(VIII)

as defined hereinbefore, which is useful as a synthesis intermediate for the synthesis of compounds of formula (I) and is useful as an AMPA receptor modulating agent, and more especially to the compound of formula (IX), a particular case of compounds of formula (VIII):

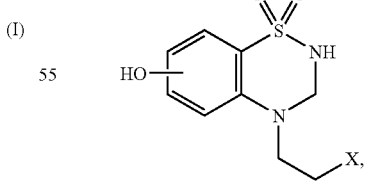
(IX)

wherein X represents a fluorine, chlorine, bromine or iodine atom, which is useful as a synthesis intermediate for the synthesis of compounds of formula (I) and is useful as an AMPA receptor modulating agent.

The invention relates also to pharmaceutical compositions comprising, as active ingredient, a compound of formula (I) or (IX) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Preparations and Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry, . . . ).

Preparation 1:

4-(2-Bromoethyl)-3,4-dihydro-2H-1,2,4-benzothiadiazin-7-ol 1,1-dioxide

Step A:

2-(7-Methoxy-1,1-dioxido-4H-1,2,4-benzothiadiazin-4-yl)ethanol

To a solution of 7-methoxy-4H-1,2,4-benzothiadiazine 1,1-dioxide (4.0 g, 18.8 mmol) in a mixture of 30 ml of DMF and 30 ml of $CH_3CN$ there are added 8.6 g (56.6 mmol) of CsF and 1.47 ml (18.8 mmol) of 2-bromoethanol. Stirring is carried out for 2 hours at 75° C. and 1.47 ml (18.8 mmol) of 2-bromoethanol are added. After 6 more hours at 75° C., a further 1.47 ml (18.8 mmol) of 2-bromoethanol and then 2.8 g (18.8 mmol) of CsF are added and stirring is continued at 75° C. overnight. The salts are filtered off at ambient temperature and rinsed with $CH_3CN$; the filtrate is evaporated to dryness. The residue is taken up in $CH_2Cl_2$, and the organic phase is washed with saturated NaCl solution and dried ($MgSO_4$). After evaporation, the sticky residue is taken up in a mixture of ethyl ether/$CH_2Cl_2$. The gum is triturated until a solid is obtained, which is filtered off to obtain the title compound.

Melting Point: 160-162° C.

Elemental Microanalysis:

|  | C | H | N | S |
|---|---|---|---|---|
| theoretical % | 46.87 | 4.72 | 10.93 | 12.51 |
| experimental % | 46.99 | 4.96 | 10.34 | 12.51 |

Step B:

4-(2-Fluoroethyl)-7-methoxy-4H-1,2,4-benzothiadiazine 1,1-dioxide

To a solution of 3.85 g (15.02 mmol) of the compound of the previous Step in 100 ml of $CH_2Cl_2$, cooled in an ice bath, there are added, dropwise, 3.97 ml (30.0 mmol) of DAST diluted with 20 ml of $CH_2Cl_2$. The reaction solution is then allowed to return to ambient temperature in about 1 hour; 100 ml of saturated NaCl solution are then poured in and the organic phase is decanted off, dried ($MgSO_4$) and evaporated in vacuo. The residue is triturated in a mixture of ethyl ether/$CH_2Cl_2$ until a solid is obtained which is filtered off to obtain the title compound.

Melting Point: 123-128° C.

Elemental Microanalysis:

|  | C | H | N | S |
|---|---|---|---|---|
| theoretical % | 46.50 | 4.29 | 10.85 | 12.42 |
| experimental % | 45.88 | 4.41 | 10.46 | 12.61 |

Step C:

4-(2-Fluoroethyl)-7-methoxy-3,4-dihydro-2H-1,2,4-benzothiadiazine 1,1-dioxide 454 mg (12.0 mmol) of $NaBH_4$, in small portions, are added to a suspension of 2.77 g (10.7 mmol) of the compound of the previous Step in 25 ml of ethanol. After stirring for 2 hours at ambient temperature, 1N HCl is added dropwise until a white precipitate forms which is filtered off in order to recover the title compound.

Melting Point: 91-93° C.

Step D:

4-(2-Bromoethyl)-3,4-dihydro-2H-1,2,4-benzothiadiazin-7-ol 1,1-dioxide 17.6 ml (17.6 mmol) of a 1M solution of $BBr_3$ in $CH_2Cl_2$ are added, dropwise, to a solution of 1.53 g (5.88 mmol) of the compound of the previous Step in 70 ml of $CH_2Cl_2$, cooled in an ice bath. The mixture is stirred overnight while being allowed to return to ambient temperature. The reaction suspension is cooled in an ice bath and 50 ml of water are added dropwise. After stirring for 30 minutes, the precipitate is filtered off, rinsed with water and dried in vacuo. The expected compound is accordingly obtained in the form of a light brown powder.

Melting Point: 144-148° C.

Preparation 2:

4-(2-Fluoroethyl)-3,4-dihydro-2H-1,2,4-benzothiadiazin-7-ol 1,1-dioxide

Step A:

4-(2-Fluoroethyl)-4H-1,2,4-benzothiadiazin-7-ol 1,1-dioxide 100 ml (950 mmol) of the complex $BF_3.Me_3S$ are introduced into a two-necked flask purged with nitrogen and connected to a trap containing sodium hypochlorite, by means of a cannula and under nitrogen pressure. Whilst stirring and under a gentle current of nitrogen there is then quickly added, in small portions, a suspension of 5.63 g (21.8 mmol) of the compound of Step B of Preparation 1 in 75 ml of $CH_2Cl_2$. The current of nitrogen is stopped and the reaction suspension is stirred overnight at ambient temperature. The reaction mixture is cooled in an ice bath, and ice and water are added. The suspension is stirred for 30 minutes, and the precipitate is filtered off and rinsed with water and with heptane. The solid is dried and recrystallised from water to yield the title compound.

Melting Point: 230-235° C.

Elemental Microanalysis:

|  | C | H | N | S |
|---|---|---|---|---|
| theoretical % | 44.26 | 3.71 | 11.47 | 13.13 |
| experimental % | 44.55 | 4.18 | 11.34 | 13.59 |

Step B:

4-(2-Fluoroethyl)-3,4-dihydro-2H-1,2,4-benzothiadiazin-7-ol 1,1-dioxide

The procedure is as in Step C of Preparation 1, starting from the compound obtained in Step A above, except that the title compound is not precipitated after addition of 1N HCl but is extracted with $CH_2Cl_2$.

Melting Point: 178-180° C.

Elemental Microanalysis:

|  | C | H | N | S |
|---|---|---|---|---|
| theoretical % | 43.90 | 4.50 | 11.38 | 13.02 |
| experimental % | 43.73 | 4.37 | 11.10 | 12.80 |

Preparation 3:

4-(2-Chloroethyl)-3,4-dihydro-2H-1,2,4-benzothiadiazin-7-ol 1,1-dioxide

Step A:

4-(2-Chloroethyl)-7-methoxy-4H-1,2,4-benzothiadiazine 1,1-dioxide

To a suspension of 1.0 g (3.90 mmol) of the compound of Step A of Preparation 1 in 20 ml of $CH_2Cl_2$ there are added, at ambient temperature, 0.1 ml of DMF and then, dropwise, a solution containing 1.42 ml (19.5 mmol) of $SOCl_2$ in 5 ml of $CH_2Cl_2$. At the end of the addition, a solution is obtained which is stirred at the reflux of $CH_2Cl_2$ for 2 hours. The $CH_2Cl_2$ is evaporated off in vacuo and the residue is taken up in a 5% solution of $NaHCO_3$. After trituration of the residue, a solid is obtained which is filtered off, rinsed with water and dried to yield the title compound.

Melting Point : 126-130° C.

Elemental Microanalysis:

|  | C | H | N | S |
|---|---|---|---|---|
| theoretical % | 43.72 | 4.04 | 10.20 | 11.67 |
| experimental % | 43.79 | 4.06 | 9.84 | 12.01 |

Step B:

4-(2-Chloroethyl)-7-methoxy-3,4-dihydro-2H-1,2,4-benzothiadiazine 1,1-dioxide Conditions and treatment identical to Step C of Preparation 1.

Melting Point: 139-143° C.

Elemental Microanalysis:

|  | C | H | N | S | Cl |
|---|---|---|---|---|---|
| theoretical % | 43.40 | 4.73 | 10.12 | 11.59 | 12.81 |
| experimental % | 43.73 | 5.05 | 9.89 | 11.07 | 13.30 |

Step C:

4-(2-Chloroethyl)-3,4-dihydro-2H-1,2,4-benzothiadiazin-7-ol 1,1-dioxide

Conditions and treatment identical to Step D of Preparation 1.

Melting point: 171-173° C.

The compounds of Examples 1-12 are obtained by an O-arylation reaction carried out on the intermediates described in Preparations 1, 2 or 3 using the appropriate boronic acid and under the reaction and treatment conditions described in Example 1 hereinbelow.

EXAMPLE 1

N-(4-{[4-(2-Bromoethyl)-1,1-dioxido-3,4-dihydro-2H-1,2,4-benzothiadiazin-7-yl]oxy}benzyl)methanesulphonamide 80 ml of $CH_2Cl_2$, 548 µl (6.79 mmol) of pyridine, 700 mg (2.29 mmol) of the compound of Preparation 1, 8 g of 4 Å molecular sieve, 786 mg (3.43 mmol) of 4-{[(methylsulphonyl)-amino]methylphenyl)boronic acid and 623 mg (3.43 mmol) of $Cu(OAc)_2$ are introduced into a 100 ml Erlenmeyer flask. The suspension is stirred vigorously at ambient temperature, the Erlenmeyer flask being left open to the air. After 4 hours 30 minutes, the reaction mixture is diluted with an additional 50 ml of $CH_2Cl_2$ and the suspension is filtered. The filtrate is evaporated to dryness and the residue is chromatographed twice on a silica column, eluting successively with $CH_2Cl_2$/MeOH (98/2) in the first chromatographic procedure and with $CH_2Cl_2$/acetone (95/5) in the second to yield the title compound.

Melting Point: 182-184° C.

Elemental Microanalysis:

|  | C | H | N | S |
|---|---|---|---|---|
| theoretical % | 41.64 | 4.11 | 8.57 | 13.08 |
| experimental % | 42.05 | 3.76 | 8.29 | 13.09 |

EXAMPLE 2

N-(4-{[14-(2-Fluoroethyl)-1,1-dioxido-3,4-dihydro-2H-1,2,4-benzothia-diazin-7-yl]oxy}benzyl)methanesulphonamide The procedure is as in Example 1, starting from the compound obtained in Preparation 2 and 4-{[(methylsulphonyl)amino]methyl}phenylboronic acid.

Melting Point: 100-102° C.

Elemental Microanalysis:

|  | C | H | N | S |
|---|---|---|---|---|
| theoretical % | 47.54 | 4.69 | 9.78 | 14.93 |
| experimental % | 47.14 | 4.97 | 9.56 | 14.99 |

EXAMPLE 3

N-(4-{[4-(2-Chloroethyl)-1,1-dioxido-3,4-dihydro-2H-1,2,4-benzothia-diazin-7-yl]oxy}benzyl)methanesulphonamide The procedure is as in Example 1, starting from the compound obtained in Preparation 3 and 4-{[(methylsulphonyl)amino]methyl}phenylboronic acid.

Melting Point: 172-175° C.

Elemental Microanalysis:

|  | C | H | N | S | Cl |
|---|---|---|---|---|---|
| theoretical % | 45.79 | 4.52 | 9.42 | 14.38 | 7.95 |
| experimental % | 45.55 | 4.84 | 9.24 | 14.69 | 8.41 |

EXAMPLE 4

N-(3-{[4-(2-Fluoroethyl)-1,1-dioxido-3,4-dihydro-2H-1,2,4-benzothia-diazin-7-yl]oxy}phenyl)methanesulphonamide The procedure is as in Example 1, starting from the compound obtained in Preparation 2 and 3-{[(methylsulphonyl)amino]phenylboronic acid.

Melting Point: 131-134° C.

Elemental Microanalysis:

|  | C | H | N | S |
|---|---|---|---|---|
| theoretical % | 46.26 | 4.37 | 10.11 | 15.44 |
| experimental % | 46.09 | 4.35 | 9.91 | 15.85 |

EXAMPLE 5

N-(4-{[4-(2-Fluoroethyl)-1,1-dioxido-3,4-dihydro-2H-1,2,4-benzothia-diazin-7-yl]oxy}phenyl)methanesulphonamide The procedure is as in Example 1, starting from the compound obtained in Preparation 2 and 4-{[(methylsulphonyl)amino]phenylboronic acid.

Melting Point: 151-152° C.

Elemental Microanalysis:

|  | C | H | N | S |
|---|---|---|---|---|
| theoretical % | 46.26 | 4.37 | 10.11 | 15.44 |
| experimental % | 45.71 | 4.78 | 9.90 | 15.65 |

EXAMPLE 6

4-(2-Fluoroethyl)-7-(3-methoxyphenoxy)-3,4-dihydro-2H-1,2,4-benzo-thiadiazine 1,1-dioxide The procedure is as in Example 1, starting from the compound obtained in Preparation 2 and 3-methoxyphenylboronic acid.

Melting Point: 101-102° C.

Elemental Microanalysis:

|  | C | H | N | S |
|---|---|---|---|---|
| theoretical % | 54.54 | 4.86 | 7.95 | 9.10 |
| experimental % | 54.50 | 4.85 | 7.77 | 8.91 |

EXAMPLE 7

N-(3-{[4-(2-Fluoroethyl)-1,1-dioxido-3,4-dihydro-2H-1,2,4-benzothia-diazin-7-yl]oxy}benzyl)acetamide The procedure is as in Example 1, starting from the compound obtained in Preparation 2 and 3-[(acetylamino)methyl]phenylboronic acid.

Melting Point: 129-131° C.

Elemental Microanalysis:

|  | C | H | N | S |
|---|---|---|---|---|
| theoretical % | 54.95 | 5.12 | 10.68 | 8.15 |
| experimental % | 55.03 | 5.18 | 10.35 | 8.22 |

EXAMPLE 8

N-(3-{[4-(2-Fluoroethyl)-1,1-dioxido-3,4-dihydro-2H-1,2,4-benzothia-diazin-7-yl]oxy}benzyl)methanesulphonamide The procedure is as in Example 1, starting from the compound obtained in Preparation 2 and 3-{[(methylsulphonyl)amino]methyl}phenylboronic acid.

Melting Point : 110-112° C.

Elemental Microanalysis:

|  | C | H | N | S |
|---|---|---|---|---|
| theoretical % | 45.54 | 4.69 | 9.78 | 14.93 |
| experimental % | 47.26 | 4.86 | 9.45 | 15.01 |

EXAMPLE 9

N-(4-{[4-(2-Fluoroethyl)-1,1-dioxido-3,4-dihydro-2H-1,2,4-benzo-thiadiazin-7-yl]oxy}benzyl)-N-methylmethanesulphonamide The procedure is as in Example 1, starting from the compound obtained in Preparation 2 and 4-{[methyl(methylsulphonyl)amino]methyl}phenyl)boronic acid.

Melting Point: 59° C.

Elemental Microanalysis:

|  | C | H | N | S |
|---|---|---|---|---|
| theoretical % | 48.75 | 5.00 | 9.47 | 14.46 |
| experimental % | 48.53 | 5.16 | 9.06 | 14.41 |

EXAMPLE 10

4-(2-Fluoroethyl)-7-phenoxy-3,4-dihydro-2H-1,2,4-benzothiadiazine 1,1-dioxide

The procedure is as in Example 1, starting from the compound obtained in Preparation 2 and phenylboronic acid.

Melting Point: 145° C.

Elemental Microanalysis:

|              | C     | H    | N    | S    |
|--------------|-------|------|------|------|
| theoretical %  | 55.89 | 4.69 | 8.69 | 9.95 |
| experimental % | 55.70 | 4.81 | 8.48 | 9.89 |

EXAMPLE 11

3-{[4-(2-Fluoroethyl)-1,1-dioxido-3,4-dihydro-2H-1,2,4-benzothiadiazin-7-yl]oxy}-N'-hydroxybenzenecarboximidamide Step A:

3-{[4-(2-Fluoroethyl)-1,1-dioxido-4H-1,2,4-benzothiadiazin-7-yl]oxy}benzonitrile The procedure is as in Example 1, starting from the compound obtained in Step A of Preparation 2 and 3-cyanophenylboronic acid and extending the reaction time to 48 hours.

Melting Point: 202-208° C.

Step B:

3-{[4-(2-Fluoroethyl)-1,1-dioxido-4H-1,2,4-benzothiadiazin-7-yl]oxy}-N'-hydroxybenzenecarboximidamide 770 µL (5.52 mmol) of triethylamine are added to a solution of hydroxylamine hydrochloride (384 mg, 5.52 mmol) in 1.8 ml of DMSO, and the suspension is stirred for 20 minutes at ambient temperature. The precipitate is filtered off and the filtrate is concentrated in vacuo. To the resulting filtrate there are added 225 mg (0.921 mmol) of the compound of Step A above and the solution is stirred at 75° C. for 4 hours. The reaction mixture is cooled to ambient temperature and the reaction mixture is precipitated from water. A white, non-filterable, gummy paste is obtained which is separated from the aqueous phase by simple decanting. The gum is triturated in ethanol until crystallisation occurs. The solid is filtered off to yield the title compound.

Melting Point: 181-183° C.

Step C:

3-{[4-(2-Fluoroethyl)-1,1-dioxido-3,4-dihydro-2H-1,2,4-benzothiadiazin-7-yl]oxy}-N'-hydroxybenzenecarboximidamide 10 mg (0.258 mmol) of $NaBH_4$ are added to a suspension of the compound obtained in Step B (75 mg, 0.198 mmol) in 1 ml of ethanol. The suspension is stirred for 30 minutes at ambient temperature and is then cooled in an ice bath. The reaction mixture is neutralised by adding 1N HCl and extracted with ethyl acetate. The organic phase is washed with saturated NaCl solution, dried ($MgSO_4$) and evaporated in vacuo. The evaporation residue is crystallised from $CH_2Cl_2$. The expected compound is recovered by filtration.

Melting Point: 160-163° C.

EXAMPLE 12

3-{[4-(2-Fluoroethyl)-1,1-dioxido-3,4-dihydro-2H-1,2,4-benzothiadiazin-7-yl]oxy}-N-methylbenzamide The procedure is as in Example 1, starting from the compound obtained in Preparation 2 and 3-[(methylamino)carbonyl]phenylboronic acid.

Melting Point: 194-196° C.

Elemental Microanalysis:

|              | C     | H    | N     | S    |
|--------------|-------|------|-------|------|
| theoretical %  | 53.82 | 4.78 | 11.08 | 8.45 |
| experimental % | 53.53 | 4.98 | 10.87 | 8.42 |

PHARMACOLOGICAL STUDY OF COMPOUNDS OF THE INVENTION

Study of the Excitatory Currents Induced by AMPA in Xenopus Oocytes a-Method:

mRNA's are prepared from cerebral cortex of male Wistar rats by the guanidinium thiocyanate/phenol/chloroform method. The poly ($A^+$) mRNA's are isolated by chromatography on oligo-dT cellulose and injected at a level of 50 ng per oocyte. The oocytes are incubated for 2 to 3 days at 18° C. to permit expression of the receptors and are then stored at 8-10° C.

Electrophysiological recording is carried out in a Plexiglass® chamber at 20-24° C. in OR2 medium (J. Exp. Zool., 1973, 184, 321-334) by the "voltage-clamp" method using two electrodes, with a third electrode placed in the bath serving as reference.

All the compounds are applied via the incubation medium and the electric current is measured at the end of the application period. AMPA is used in a concentration of 10 µM. For each compound studied, the concentration that doubles (EC2X) or quintuples (EC5X) the intensity of the current induced by AMPA alone (5 to 50 nA) is determined.

b-Results:

The compounds of the invention potentiate the excitatory effects of AMPA to a very considerable degree and their activity is very clearly superior to that of compounds of reference.

By way of example, the compound of Example 1 has an EC2X of 0.04 µM.

PHARMACEUTICAL COMPOSITION

| Formula for the preparation of 1000 tablets each containing 100 mg of N-(4-{[4-(2-fluoroethyl)-1,1-dioxido-3,4-dihydro-2H-1,2,4-benzothiadiazin-7-yl]oxy}benzyl)methanesulphonamide (Example 2) | 100 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

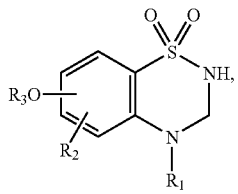

wherein:
- $R_1$ represents linear or branched ($C_1$-$C_6$)alkyl substituted by one or more halogen atoms,
- $R_2$ represents hydrogen, halogen or hydroxy,
- $R_3$ represents unsubstituted aryl or aryl substituted by one or more identical or different groups selected from:
  linear or branched ($C_1$-$C_6$)alkyl; linear or branched ($C_1$-$C_6$)alkoxy; linear or branched ($C_1$-$C_6$)polyhaloalkyl; halogens; linear or branched ($C_1$-$C_6$)alkoxycarbonyl; linear or branched ($C_1$-$C_6$)alkylthio; carboxy; linear or branched ($C_1$-$C_6$)acyl; linear or branched ($C_1$-$C_6$)polyhaloalkoxy; hydroxy; cyano; nitro; amidino, optionally substituted by one or two identical or different groups selected from linear or branched ($C_1$-$C_6$)alkyl, hydroxy, linear or branched ($C_1$-$C_6$)alkoxy and

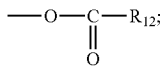

amino, optionally substituted by one or two linear or branched ($C_1$-$C_6$)alkyl; aminocarbonyl, optionally substituted by one or two linear or branched ($C_1$-$C_6$)alkyl; benzyloxy; ($C_1$-$C_6$)alkylsulphonylamino, optionally substituted on the nitrogen by linear or branched ($C_1$-$C_6$)alkyl; trifluoromethylsulphonylamino; a heterocyclic group; and linear or branched ($C_1$-$C_6$)alkyl substituted by one or more identical or different groups selected from halogen, linear or branched ($C_1$-$C_6$)alkyl, $NR_4R_5$, $S(O)_nR_6$, $OR_7$, amidino, optionally substituted by one or two identical or different groups selected from linear or branched ($C_1$-$C_6$)alkyl, hydroxy, linear or branched ($C_1$-$C_6$)alkoxy and

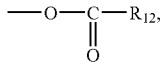

and a heterocyclic group, wherein:
- $R_4$ represents hydrogen, linear or branched ($C_1$-$C_6$)alkyl, $S(O)_pR_8$, $COR_9$ or $P(O)(OR_{10})(OR_{11})$,
- $R_5$ represents hydrogen, linear or branched ($C_1$-$C_6$)alkyl, or $R_4$ and $R_5$, together with the nitrogen atom carrying them, form a heterocyclic group,
- $R_6$, $R_8$, $R_9$, $R_{10}$, $R_{11}$ and $R_{12}$, which may be the same or different, each represent hydrogen or linear or branched ($C_1$-$C_6$)alkyl optionally substituted by one or more halogen atoms; aryl-($C_1$-$C_6$)alkyl wherein the alkyl moiety is linear or branched; or aryl,
- $R_7$ represents linear or branched ($C_1$-$C_6$)alkyl or linear or branched ($C_1$-$C_6$)acyl, n and p, which may be the same or different, each represent 0, 1 or 2, its enantiomers and diastereoisomers, and addition salts thereof with a pharmaceutically-acceptable acid or base.

2. A compound of claim 1, wherein $R_1$ represents haloethyl.

3. A compound of claim 1, wherein $R_2$ represents hydrogen.

4. A compound of claim 1, wherein $R_3$ represents unsubstituted phenyl.

5. A compound of claim 1, wherein $R_3$ represents phenyl substituted by amidino, hydroxyamidino, alkoxy, alkylsulphonylamino, optionally substituted on the nitrogen by alkyl, or alkyl substituted by amidino, hydroxyamidino, $OR_7$, $NH(SO)_pR_8$ or $NHCOR_9$.

6. A compound of claim 1, which is selected from:
   N-(4-{[4-(2-fluoroethyl)-1,1-dioxido-3,4-dihydro-2H-1,2,4-benzothiadiazin-7-yl]oxy}benzyl)methanesulphonamide and
   N-(4-{[4-(2-chloroethyl)-1,1-dioxido-3,4-dihydro-2H-1,2,4-benzothiadiazin-7-yl]oxy}benzyl)methanesulphonamide, and addition salts thereof with a pharmaceutically-acceptable acid or base.

7. A process for the synthesis of a compound selected from those of formula (I) of claim 1, comprising reaction of a compound selected from those of formula (VIII):

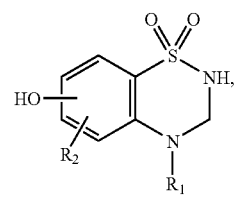

wherein $R_1$ represents linear or branched ($C_1$-$C_6$) alkyl substituted by one or more halogen atoms and $R_2$ represents hydrogen, halogen or hydroxyl, with a compound selected from those of formula (V):

$R_3$—$B(OH)_2$       (V), wherein
- $R_3$ represents unsubstituted aryl or aryl substituted by one or more identical or different groups selected from:
  linear or branched ($C_1$-$C_6$)alkyl; linear or branched ($C_1$-$C_6$)alkoxy; linear or branched ($C_1$-$C_6$)polyhaloalkyl; halogens; linear or branched ($C_1$-$C_6$)alkoxy-carbonyl; linear or branched ($C_1$-$C_6$)alkylthio; carboxy; linear or branched ($C_1$-$C_6$)acyl; linear or branched ($C_1$-$C_6$)polyhaloalkoxy; hydroxy; cyano; nitro; amidino, optionally substituted by one or two identical or different groups selected from linear or branched ($C_1$-$C_6$)alkyl, hydroxy, linear or branched ($C_1$-$C_6$)alkoxy and

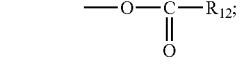

amino, optionally substituted by one or two linear or branched ($C_1$-$C_6$)alkyl; aminocarbonyl, optionally substituted by one or two linear or branched ($C_1$-$C_6$)alkyl; benzyloxy; ($C_1$-$C_6$)alkylsulphonylamino, optionally substituted on the nitrogen by linear or branched ($C_1$-$C_6$)alkyl; trifluoromethylsulphonylamino; a heterocyclic group ; and linear or branched ($C_1$-$C_6$)alkyl substituted by one or more identical or different groups selected from halogen, linear or branched ($C_1$-$C_6$)alkyl, $NR_4R_5$, $S(O)_nR_6$, $OR_7$, amidino, optionally substituted by one or two identical or different groups selected from linear or branched ($C_1$-$C_6$)alkyl, hydroxy, linear or branched ($C_1$-$C_6$)alkoxy and

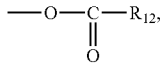

and a heterocyclic group, wherein:
- $R_4$ represents hydrogen, linear or branched ($C_1$-$C_6$)alkyl, $S(O)_pR_8$, $COR_9$ or $P(O)(OR_{10})(OR_{11})$,
- $R_5$ represents hydrogen, linear or branched ($C_1$-$C_6$)alkyl, or $R_4$ and $R_5$, together with the nitrogen atom carrying them, form a heterocyclic group,
- $R_6$, $R_8$, $R_9$, $R_{10}$, $R_{11}$ and $R_{12}$, which may be the same or different, each represent hydrogen or linear or branched ($C_1$-$C_6$)alkyl optionally substituted by one or more halogen atoms; aryl-($C_1$-$C_6$)alkyl wherein the alkyl moiety is linear or branched; or aryl,
- $R_7$ represents linear or branched ($C_1$-$C_6$)alkyl or linear or branched ($C_1$-$C_6$)acyl, and n and p, which may be the same or different, each represent 0, 1 or 2, to yield a compound selected from those of formula (I), which compound may be further purified, and which compound may be converted, if desired, into an addition salt thereof with a pharmaceutically acceptable acid.

8. A process for the synthesis of a compound selected from those of formula (I) of claim 1, comprising reaction of a compound selected from those of formula (IX):

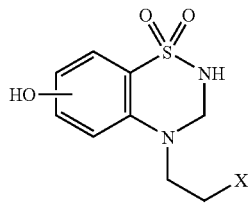

(IX)

wherein X represents a fluorine, chlorine, bromine or iodine atom, with a compound selected from those of formula (V):

$R_3$—B(OH)$_2$ (V), wherein
- $R_3$ represents unsubstituted aryl or aryl substituted by one or more identical or different groups selected from: linear or branched ($C_1$-$C_6$)alkyl; linear or branched ($C_1$-$C_6$)alkoxy; linear or branched ($C_1$-$C_6$)polyhaloalkyl; halogens; linear or branched ($C_1$-$C_6$)alkoxy-carbonyl; linear or branched ($C_1$-$C_6$)alkylthio; carboxy; linear or branched ($C_1$-$C_6$)acyl; linear or branched ($C_1$-$C_6$)polyhaloalkoxy; hydroxy; cyano; nitro; amidino, optionally substituted by one or two identical or different groups selected from linear or branched ($C_1$-$C_6$)alkyl, hydroxy, linear or branched ($C_1$-$C_6$)alkoxy and

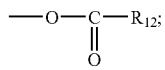

amino, optionally substituted by one or two linear or branched ($C_1$-$C_6$)alkyl; aminocarbonyl, optionally substituted by one or two linear or branched ($C_1$-$C_6$)alkyl; benzyloxy; ($C_1$-$C_6$)alkylsulphonylamino, optionally substituted on the nitrogen by linear or branched ($C_1$-$C_6$)alkyl; trifluoromethylsulphonylamino; a heterocyclic group ; and linear or branched ($C_1$-$C_6$)alkyl substituted by one or more identical or different groups selected from halogen, linear or branched ($C_1$-$C_6$)alkyl, $NR_4R_5$, $S(O)_nR_6$, $OR_7$, amidino, optionally substituted by one or two identical or different groups selected from linear or branched ($C_1$-$C_6$) alkyl, hydroxy, linear or branched ($C_1$-$C_6$)alkoxy and

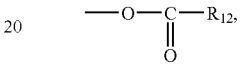

and a heterocyclic group, wherein:
- $R_4$ represents hydrogen, linear or branched ($C_1$-$C_6$)alkyl, $S(O)_pR_8$, $COR_9$ or $P(O)(OR_{10})(OR_{11})$,
- $R_5$ represents hydrogen, linear or branched ($C_1$-$C_6$)alkyl, or $R_4$ and $R_5$, together with the nitrogen atom carrying them, form a heterocyclic group,
- $R_6$, $R_8$, $R_9$, $R_{10}$, $R_{11}$ and $R_{12}$, which may be the same or different, each represent hydrogen or linear or branched ($C_1$-$C_6$)alkyl optionally substituted by one or more halogen atoms; aryl-($C_1$-$C_6$)alkyl wherein the alkyl moiety is linear or branched; or aryl,
- $R_7$ represents linear or branched ($C_1$-$C_6$)alkyl or linear or branched ($C_1$-$C_6$)acyl, and n and p, which may be the same or different, each represent 0, 1 or 2, to yield a compound selected from those of formula (I), which compound may be further purified, and which compound may be converted, if desired, into an addition salt thereof with a pharmaceutically acceptable acid.

9. A pharmaceutical composition comprising as active principle an effective amount of a compound of claim 1, together with one or more pharmaceutically-acceptable excipients or vehicles.

10. A method for treating a living animal body, including a human, afflicted with a condition selected from anxiety and depression, comprising the step of administering to the living animal body, including a human, an amount of a compound of claim 1, which is effective for alleviation of the condition.

* * * * *

UNITED STATES PATENT AND TRADEMARK OFFICE
CERTIFICATE OF CORRECTION

| | |
|---|---|
| PATENT NO. | : 7,268,130 B2 |
| APPLICATION NO. | : 11/265011 |
| DATED | : September 11, 2007 |
| INVENTOR(S) | : Patrice Desos et al. |

Page 1 of 1

It is certified that error appears in the above-identified patent and that said Letters Patent is hereby corrected as shown below:

Title Page;
Please add: "(30) Foreign Application Priority Date November 3, 2004 (FR) 04.11690"

Signed and Sealed this

Twenty-first Day of April, 2009

JOHN DOLL
*Acting Director of the United States Patent and Trademark Office*